(12) United States Patent
Skaggs

(10) Patent No.: US 8,454,610 B2
(45) Date of Patent: Jun. 4, 2013

(54) ORTHOPEDIC SURGICAL DEVICE

(75) Inventor: David L. Skaggs, Los Angeles, CA (US)

(73) Assignee: EBI, LLC, Parsippany, NJ (US)

( * ) Notice: Subject to any disclaimer, the term of this patent is extended or adjusted under 35 U.S.C. 154(b) by 21 days.

(21) Appl. No.: 12/829,309

(22) Filed: Jul. 1, 2010

(65) Prior Publication Data

US 2011/0004214 A1    Jan. 6, 2011

Related U.S. Application Data

(60) Provisional application No. 61/222,210, filed on Jul. 1, 2009.

(51) Int. Cl.
*A61B 17/16*      (2006.01)

(52) U.S. Cl.
USPC ............................................. 606/84; 606/172

(58) Field of Classification Search
USPC ............. 606/79, 82–85, 86 R, 167, 170, 172, 606/184–185; 30/167, 167.1, 167.2, 168
See application file for complete search history.

(56) References Cited

U.S. PATENT DOCUMENTS

| | | | |
|---|---|---|---|
| 622,461 A * | 4/1899 | Glardon-Jacquet et al. ..... 142/56 |
| 4,239,045 A | 12/1980 | Schlein | |
| 4,586,496 A | 5/1986 | Keller | |
| 5,437,675 A | 8/1995 | Wilson | |
| 6,110,175 A * | 8/2000 | Scholl .............................. 606/79 |
| 6,391,031 B1 | 5/2002 | Toomey | |
| 2005/0090829 A1* | 4/2005 | Martz et al. ...................... 606/79 |
| 2005/0251146 A1* | 11/2005 | Martz et al. ...................... 606/84 |
| 2006/0095042 A1* | 5/2006 | Malkani ........................... 606/86 |

FOREIGN PATENT DOCUMENTS

JP       08126647 A   *   5/1996

* cited by examiner

*Primary Examiner* — Kevin T Truong
*Assistant Examiner* — Larry E Waggle, Jr.
(74) *Attorney, Agent, or Firm* — Harness, Dickey

(57) ABSTRACT

An osteotome may include a handle; a shaft coupled to the handle; a cutting member coupled to the shaft, wherein the cutting member comprises a first cutting surface positioned perpendicular to a second cutting surface, and wherein said first and second cutting surfaces extend downward relative to the shaft; and a stop means configured to control the depth of cut by the cutting member.

19 Claims, 3 Drawing Sheets

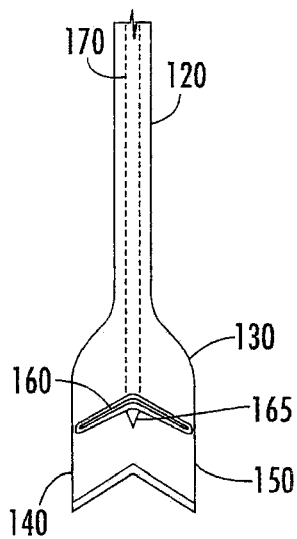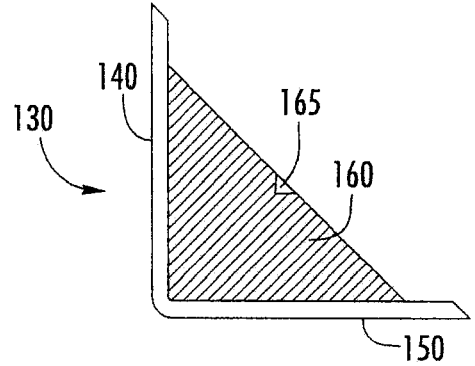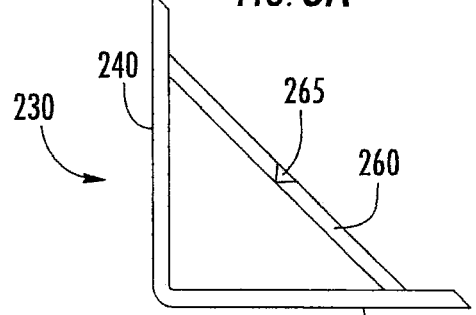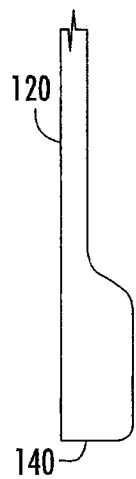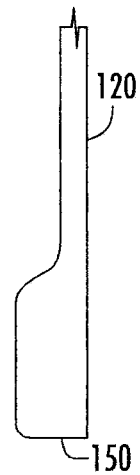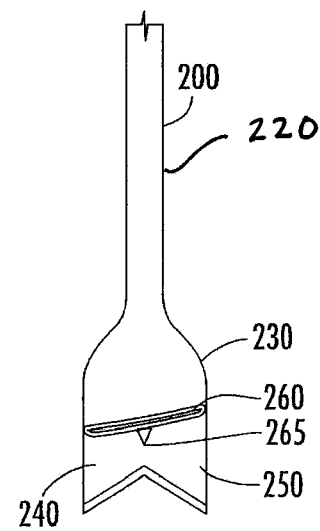

ORTHOPEDIC SURGICAL DEVICE

CROSS-REFERENCE TO RELATED APPLICATIONS

This application claims the benefit of priority to U.S. Provisional Application No. 61/222,210, filed on Jul. 1, 2009, which is herein incorporated by reference in its entirety.

FIELD

This disclosure is directed to surgical devices and, more particularly, to osteotomes that avoid unintentional entrance into vital areas around the excision site.

BACKGROUND

Facetectomies involve decompression of the spinal nerve root by removal of a spinal facet or a part thereof. Facetectomy surgeries are often performed to treat orthopedic conditions, such as spondylolisthesis, cervical rhizalgia, and nerve root compression due to facet joint degeneration. Current surgical tools used to perform facetectomies include osteotomes, which are driven into the bone by manual or mechanical means at the surgical site to excise a spinal facet or part thereof. A drawback to current osteotomes is the risk of nerve damage due to the possibility that the osteotome will inadvertently advance too deeply past the bone into the spinal canal, potentially damaging vital structures such as the spinal cord.

Additionally, some current surgical tools require multiple steps to remove the bone, and do not remove a sufficient amount of bone in a single step. For example, rounded gauges may perform a semicircular in the bone facet, but such tools do not prevent inadvertent entrance into the neural canal or other vital structures. They also do not remove as much of the facet joint as two cuts from a standard osteotome or one cut from a 90° osteotome. Likewise, power burrs are power instruments (e.g., Midas Rex M-8) used to remove facet joints but these instruments do not prevent inadvertent entrance into the neural canal or other critical areas. Using a power burr requires more time, can cause more bleeding, and/or is more difficult to define and preserve the remaining superior facet compared to osteotomes. Preserving the remaining superior facet is important, as this serves as a landmark for placement of surgical devices, such as pedicle screws.

There is a need in the art for an improved surgical device that allows safer, more controlled bone excision, prevents accidental entrance into vital areas around the excision site, does not require multiple steps to remove bone, and removes a sufficient amount of bone in one step.

SUMMARY OF THE INVENTION

Exemplary embodiments according to aspects of the present invention may satisfy one or more of the above-mentioned desirable features set forth above. Other features and advantages will become apparent from the following detailed description.

In accordance with various exemplary embodiments, the invention may include an osteotome having a handle; a shaft coupled to the handle; a cutting member coupled to the shaft, wherein the cutting member comprises a first cutting surface positioned perpendicular to a second cutting surface, and wherein said first and second cutting surfaces extend longitudinally relative to the shaft; and a stop means configured to control the depth of cut by the cutting member.

According to various embodiments, the stop means can be moveable and can be positioned between the first and second cutting surfaces. According to another embodiment, the osteotome can have a moveable plunger coupled to the stop means. In yet another embodiment, a spike can be coupled to the stop means. According to yet further embodiments, the stop means can be affixed to the first and second cutting surfaces and is not moveable.

According to various exemplary embodiments, a rotatable member can be coupled to the moveable plunger. In another embodiment, the osteotome can have a locking means to render the plunger and stop means immovable.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the invention.

BRIEF DESCRIPTION OF THE DRAWINGS

The drawings of this application illustrate exemplary embodiments of the invention and together with the written description, serve to explain certain features. In the drawings:

FIG. 2 illustrates a front view of an exemplary osteotome according to the present disclosure.

FIG. 3 illustrates an end-on view of an osteotome according to the present disclosure.

FIGS. 4A-4B illustrate side views of an osteotome according to the present disclosure.

FIG. 5 illustrates a partial front view of another exemplary osteotome according to the present disclosure.

DESCRIPTION OF VARIOUS EMBODIMENTS

Figure 1:
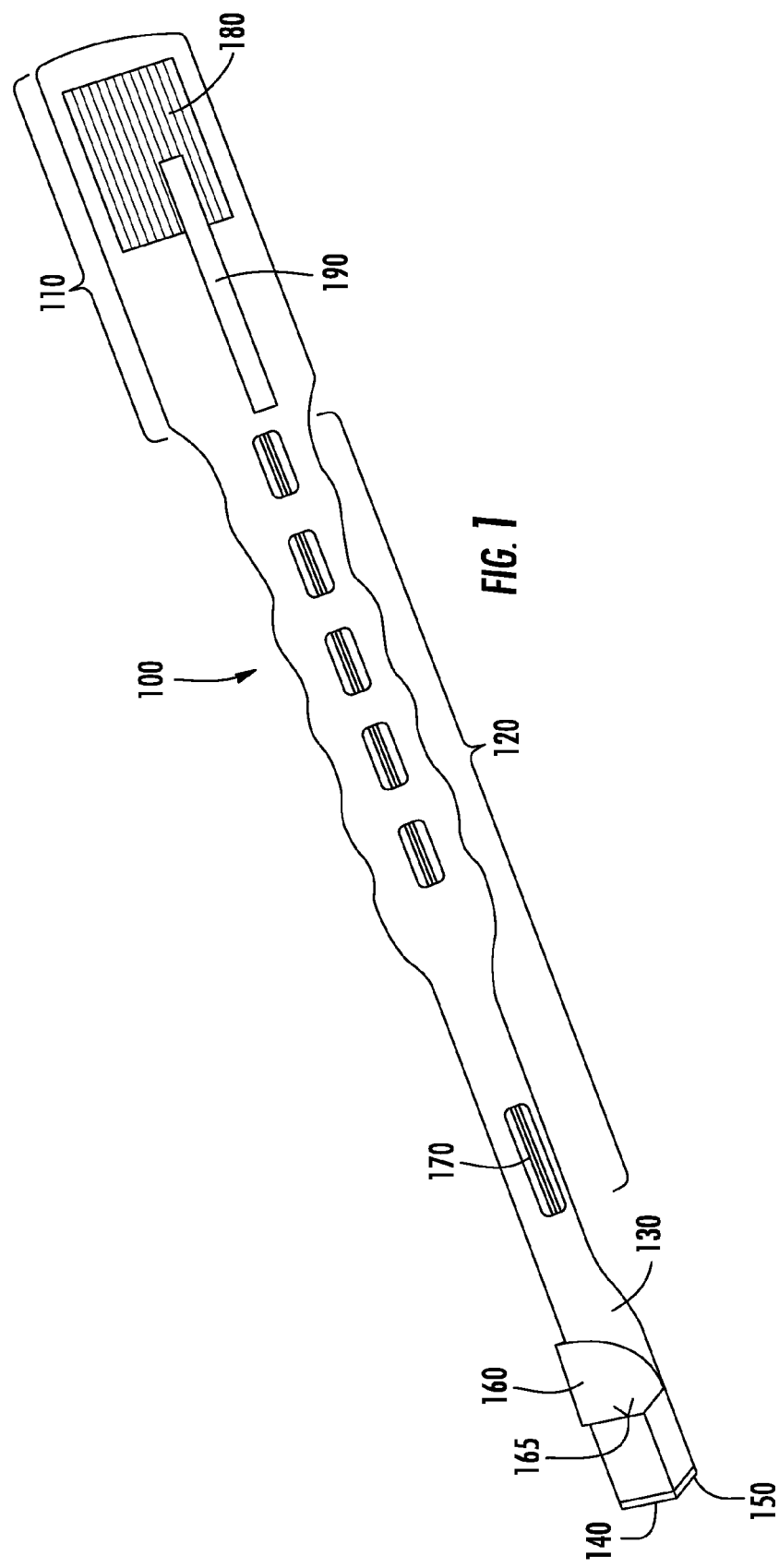
FIG. 1 illustrates a perspective view of an osteotome according to the present disclosure.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose. In the event that one or more of the incorporated literature and similar materials differs from or contradicts this application, including but not limited to defined terms, term usage, described techniques, or the like, this application controls.

When referring to various directional relationships herein, for example, distally, proximally, downward, upward, left, right, top, bottom, etc., such relationships are referred to in the context of the orientation of the drawings, unless otherwise specified. It should be understood, however, that the devices in actuality may be oriented in directions other than those illustrated in the drawings and directional relationships would vary accordingly.

Reference will now be made to various embodiments, examples of which are illustrated in the accompanying drawings. However, it will be understood that these various embodiments are not intended to limit the disclosure. On the contrary, the disclosure is intended to cover alternatives, modifications, and equivalents.

Exemplary aspects of the disclosure provide an osteotome. FIG. 1 shows an illustrative embodiment osteotome 100 including a handle 110, a shaft 120 coupled to the handle 110, a cutting member 130 coupled to the shaft 120, and a stop means 160 configured to control the depth of cut by the cutting member 130. The cutting member 130 can have a first cutting surface 140 positioned perpendicular to a second cutting 150 surface such that the first and second cutting surfaces 140,150 form a right angle (about 90°). The first and second cutting surfaces 140,150 can extend downward relative to the shaft 120. The first and second cutting surfaces 140,150 can have beveled cutting edges for cutting accuracy at an excision site (e.g., bone excision site). In an aspect, the beveled cutting edges of the first and second cuffing surfaces 140, 150 extend away from to the shaft 120.

The stop means 160 can be coupled to a moveable plunger 170. The moveable plunger 170 can extend through the shaft 120 (for example, a hollow shaft) into the handle 110. In an aspect, a rotatable member 180 can be coupled to the moveable plunger 170. The rotatable member 180 can be configured to adjust the stop means longitudinally relative to the first and second cutting surfaces 140,150. For example, the rotatable member 180 can be configured such that the moveable plunger 170 can advance the stop means 160 towards the beveled cutting edges of the first and second cutting surfaces 140,150 when rotated in one direction, and can retract the stop means 160 towards the shaft when rotated in the opposite direction. In this way, the depth of cut can be controlled by the stop means 160. When manual or mechanical force is applied to the osteotome and the device is driven into the bone, for example an interior facet joint, the osteotome cannot advance more than the allowed distance per the stop means 160. The stop means 160 blocks further advancement of the osteotome beyond the distance determined by the stop means 160. Thus, the stop means 160 can prevent inadvertent entry of the osteotome into the spinal column during surgical procedures, such as a facetectomy, and avoid potential damage to vital structures, such as the spinal cord. In an aspect, the stop means 160 can be made of a transparent material. In another aspect, the stop means 160 can have a concave shape.

In a further aspect, a locking means 190 can be coupled to the rotatable member 180. The locking means 190 can be configured to render the moveable plunger 170 and stop means 160 immovable. Once the locking means 190 is engaged, the stop means 160 is in a fixed position and locked at a certain depth (immovable). This prevents further advancement of the osteotome beyond the distance established by the stop means 160 when the osteotome is driven into the bone. In an embodiment, the locking means 190 can also be coupled to the handle 110.

In yet another embodiment, a spike 165 can be coupled to the stop means 160. As the osteotome 100 is driven into bone, the spike 165 can enter the bone portion to be removed and fasten the bone portion to the stop means 160. After the bone portion is detached from the remaining posterior elements of the spine, the bone portion can be removed from the stop means 160.

FIG. 2 illustrates a front view of the osteotome 100 having a shaft 120; a moveable plunger 170 located inside the shaft 120; a cutting member 130 (having a first and second cutting surface 140,150) coupled to the shaft; and a stop means 160. The depth of cut can be controlled by moving the stop means 160 up or down.

FIG. 3 illustrates an end-on view of the osteotome. In the cutting head 130, the first cutting surface 140 is positioned perpendicular to the second cutting 150 surface such that the first and second cutting surfaces 140, 150 form a right angle. The stop means 160 is positioned between the first and second cutting surfaces 140, 150 in the cutting member 130. A spike 165 is coupled to the stop means 160.

FIGS. 4A-4B illustrate side views of the osteotome. FIG. 4A illustrates one side of the osteotome having a shaft 120 coupled to the cutting member 130, and showing a first cutting surface 140. FIG. 4B illustrates another side of the osteotome having a shaft 120 coupled to the cutting member 130, and showing a second cutting surface 150.

Another exemplary aspect of the disclosure provides an osteotome having the cutting member 130, the shaft 120, and the stop means 160 in a fixed relationship relative to each other—e.g., without moving parts. The cutting member 130, the shaft 120, and the stop means 160 are not moveable. FIG. 5 shows a partial front end view of such an osteotome 200. The partial front end view shows the osteotome shaft 220 coupled to the cutting member 230, and a stop means 260 coupled to the cutting member 230. The stop means 260 can be affixed to the first and second cutting surfaces 240,250 such that the stop means 260 bridges the space between the first and second cutting surfaces 240,250. As such, the stop means 260 is configured to control the depth of cut by the cutting member 230. In an aspect, the stop means 260 can be bar-shaped. In another aspect, a spike 265 can be coupled to the stop means 260.

Figure 6:
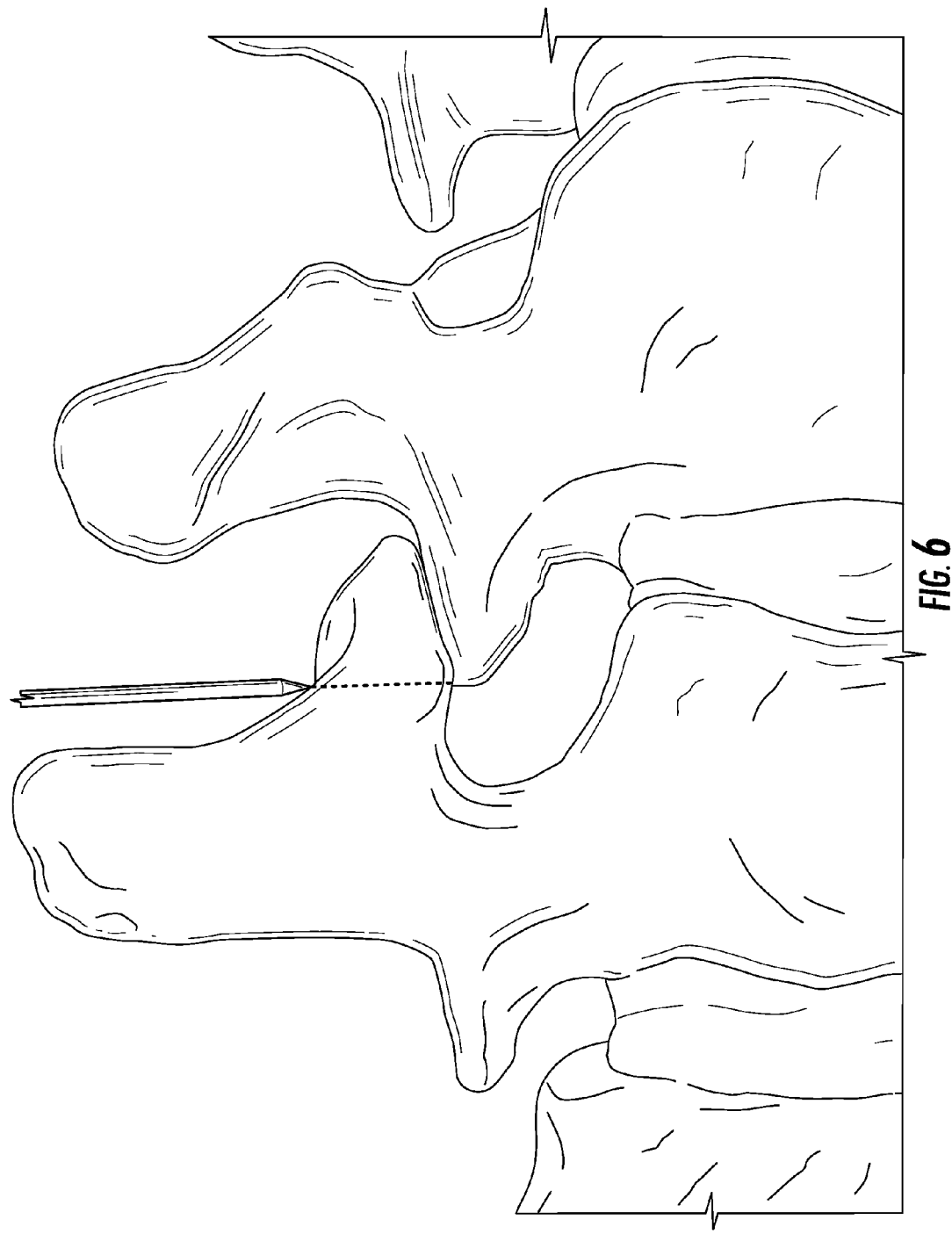
FIG. 6 illustrates a partial perspective view of an osteotome according to the present disclosure.

FIG. 6 shows a partial perspective view of an osteotome cutting into an interior facet joint. The depth of cut is determined by the stop means 260. The osteotome cannot advance more than the allowed distance per the stop means 260. Thus, the stop means 260 can prevent inadvertent entry of the osteotome into the spinal column and avoid potential damage the spinal cord.

The disclosed osteotome can be driven into bone by manual force, such as hitting it with a hammer, mallet, or like object to provide force to the osteotome to cut the bone. Alternatively, the disclosed osteotome can be driven into bone by mechanical force, such as a motor—e.g., a power tool. The disclosed osteotome can be used as part of a surgical kit, such as a minimally invasive system having minimally invasive access instruments. The disclosed osteotome can be used in animals and/or humans. In an aspect, the osteotome can be used for thoracic and/or lumbar facets, and cervical and/or sacral facet joints. In another aspect, the osteotome can be used in non-medical settings for cutting non-biological tissue.

The disclosed osteotomes can be made of any desired material with appropriate strength, manufacturability, autoclavability, cost, and other desired performance factors. A preferred embodiment is formed from surgical grade stainless steel, but other metal and/or plastic materials may be used, and combinations of materials may be used, so long as the materials are visible under imaging, such as fluoroscopy. For example, the cutting member, shaft, stop means, and/or handle can be made of surgical grade (e.g., Grade 304) stainless steel, titanium, or other metals and metal alloys. The moveable plunger, stop means, locking means, rotatable member, and/or handle can be made of an optically transparent or opaque plastic.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a biological" includes two or more different biological samples. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the sample preparation device and method of the present disclosure without departing from the scope its teachings. Other embodiments of the disclosure will be apparent to those skilled in the art from consideration of the specification and practice of the teachings disclosed herein. It is intended that the specification and examples be considered as exemplary only.

What is claimed is:

1. An osteotome comprising:
a handle;
a shaft coupled to the handle;
a cutting member coupled to the shaft, wherein the cutting member comprises a first cutting surface positioned perpendicular to a second cutting surface, and wherein said first and second cutting surfaces extend downward relative to the shaft; and
a stop extending between and connecting the first cutting surface and the second cutting surface, the stop operable to control the depth of cut by the cutting member, wherein the stop is moveable.

2. The osteotome of claim 1, wherein the stop has a concave shape.

3. The osteotome of claim 1, further comprising a moveable plunger coupled to the stop.

4. The osteotome of claim 3, further comprising a spike coupled to the stop.

5. The osteotome of claim 3, further comprising a rotatable member coupled to the moveable plunger, wherein the rotatable member is configured to adjust the stop longitudinally relative to said first and second cutting surfaces.

6. The osteotome of claim 3, further comprising a locking means configured to render said plunger and stop immovable.

7. The osteotome of claim 6, wherein the locking means is coupled to the handle.

8. The osteotome of claim 1, wherein the stop cooperates with the first and second cutting surfaces to provide the osteotome with a substantially triangular cross-section at the stop.

9. The osteotome of claim 8, wherein the stop is recessed from a distal end of the first cutting surface and the second cutting surface.

10. The osteotome of claim 8, wherein the stop defines an opening bounded by the first cutting surface, the second cutting surface, and the stop.

11. The osteotome of claim 8, wherein the stop is attached to the first cutting surface and the second cutting surface at a junction of the first cutting surface and the second cutting surface.

12. The osteotome of claim 11, wherein the stop extends in a direction away from the junction along a length of the first cutting surface.

13. The osteotome of claim 12, wherein the stop extends in a direction away from the junction along a length of the second cutting surface.

14. The osteotome of claim 1, wherein the stop is recessed from a distal end of the first cutting surface and the second cutting surface.

15. The osteotome of claim 1, wherein the stop defines an opening bounded by the first cutting surface, the second cutting surface, and the stop.

16. The osteotome of claim 1, wherein the stop is attached to the first cutting surface and the second cutting surface at a junction of the first cutting surface and the second cutting surface.

17. The osteotome of claim 16, wherein the stop extends in a direction away from the junction along a length of the first cutting surface.

18. The osteotome of claim 17, wherein the stop extends in a direction away from the junction along a length of the second cutting surface.

19. The osteotome of claim 1, wherein the stop is formed at an acute angle relative to the first cutting surface and relative to the second cutting surface.

* * * * *